(12) United States Patent
Komeilipoor

(10) Patent No.: US 12,395,799 B2
(45) Date of Patent: Aug. 19, 2025

(54) MULTIMODAL HEARING ASSISTANCE DEVICES AND SYSTEMS

(71) Applicant: TANDEMLAUNCH INC., Montreal (CA)

(72) Inventor: Naeem Komeilipoor, Montreal (CA)

(73) Assignee: AAVAA Inc., Montreal (CA)

( * ) Notice: Subject to any disclaimer, the term of this patent is extended or adjusted under 35 U.S.C. 154(b) by 58 days.

(21) Appl. No.: 17/928,383

(22) PCT Filed: May 28, 2021

(86) PCT No.: PCT/CA2021/050730
§ 371 (c)(1),
(2) Date: Nov. 29, 2022

(87) PCT Pub. No.: WO2021/237368
PCT Pub. Date: Dec. 2, 2021

(65) Prior Publication Data
US 2023/0199413 A1 Jun. 22, 2023

Related U.S. Application Data

(60) Provisional application No. 63/032,307, filed on May 29, 2020.

(51) Int. Cl.
*H04R 25/00* (2006.01)
*A61B 5/369* (2021.01)
(Continued)

(52) U.S. Cl.
CPC .......... *H04R 25/507* (2013.01); *A61B 5/369* (2021.01); *A61B 5/398* (2021.01); *G06F 3/012* (2013.01);
(Continued)

(58) Field of Classification Search
CPC .. H04R 25/507; H04R 25/405; H04R 25/407; H04R 2225/43; A61B 5/398;
(Continued)

(56) References Cited

U.S. PATENT DOCUMENTS 11,297,448 B2 * 4/2022 Lunner ................. A61B 5/372
2012/0177233 A1 7/2012 Kidmose et al.
(Continued)

OTHER PUBLICATIONS

International Search Report; Canadian Intellectual Property Office; International Application No. PCT/CA2021/050730; Aug. 4, 2021; 3 pages.
(Continued)

*Primary Examiner* — Andrew Sniezek
(74) *Attorney, Agent, or Firm* — Taft Stettinius & Hollister LLP

(57) ABSTRACT

Hearing assistance systems, devices and methods including obtaining, by the device, multiple brain and bio-signals indicative of the auditory and visual attentional focus of the user, obtaining a mixed sound signal from multiple sound sources and applying, by the device, speech-separation and enhancement processing to the mixed sound signal to derive a plurality of separated signals that each contains signals corresponding to different groups of the multiple sound sources, and selecting one of the pluralities of separated signals either solely based on the obtained brain signals, or on a combination of bio-signals, including but not limited to eye gaze direction, head, neck and trunk orientation, etc. The separated signals may then be processed (i.e., amplified, attenuated) based on the needs of the user.

20 Claims, 3 Drawing Sheets

(51) Int. Cl.
  *A61B 5/398* (2021.01)
  *G06F 3/01* (2006.01)
  *G10L 21/028* (2013.01)
  *G10L 25/30* (2013.01)

(52) U.S. Cl.
  CPC .............. *G06F 3/013* (2013.01); *G06F 3/015* (2013.01); *G10L 21/028* (2013.01); *G10L 25/30* (2013.01); *H04R 25/405* (2013.01); *H04R 25/407* (2013.01); *H04R 2225/43* (2013.01)

(58) Field of Classification Search
  CPC ......... A61B 5/369; G06F 3/012; G06F 3/013; G06F 3/015; G10L 21/028; G10L 25/30
  See application file for complete search history.

(56) References Cited

U.S. PATENT DOCUMENTS

| | | |
|---|---|---|
| 2016/0119726 A1 | 4/2016 | Pontoppidan et al. |
| 2018/0014130 A1* | 1/2018 | Lunner ................ H04R 25/554 |
| 2018/0270571 A1 | 9/2018 | Di Censo et al. |
| 2019/0041978 A1* | 2/2019 | Loh ....................... G06F 3/0346 |
| 2019/0066713 A1 | 2/2019 | Mesgarani et al. |
| 2019/0132685 A1 | 5/2019 | Skoglund et al. |
| 2019/0253793 A1 | 8/2019 | Pedersen et al. |

OTHER PUBLICATIONS

Written Opinion of the International Searching Authority; Canadian Intellectual Property Office; International Application No. PCT/CA2021/050730; Aug. 4, 2021; 4 pages.

Extended European Search Report; European Patent Office; European Patent Application No. 21812211.7; May 21, 2024; 7 pages.

Communication Pursuant to Article 94(3) EPC; European Patent Office; European Patent Application No. 21812211.7; Apr. 2, 2025; 5 pages.

Ali Aroudi et al.; Improving Auditory Attention Decoding Performance of Linear and Non-Linear Methods Using State-Space Model; ICASSP; 2020; 6 pages.

Waldo Nogueira et al.; Towards Decoding Selective Attention From Single-Trial EEG Data in Cochlear Implant Users Based on Deep Neural Networks; ICASSP; 2020; 6 pages.

* cited by examiner

MULTIMODAL HEARING ASSISTANCE DEVICES AND SYSTEMS

CROSS REFERENCE TO RELATED APPLICATIONS

This application is a U.S. National Phase of International PCT Application No. PCT/CA2021/050730 filed May 28, 2021, which claims the benefit of U.S. Provisional Patent Application No. 63/032,307 filed May 29, 2020, the contents of each application are incorporated herein by reference in its entirety.

FIELD OF THE DESCRIPTION

The following relates to multimodal-hearing devices and systems for obtaining and analyzing the data collected from these devices using signal processing methods and machine learning approaches.

BACKGROUND

Significant efforts have been made to develop hearing devices that adapt dynamically to a wearer's listening intention by interpreting cues not only from the user's audio environment, but also from the user herself/himself. Over the past decade, strategies to steer acoustic processing such as amplifying sound sources in the direction of the user's eye gaze (e.g., Hart et al. 2009; Kidd 2017: Kidd et al. 2013), amplifying sound sources based on the direction of the user's head orientation (e.g., Favre-Félix et al. 2018), and other promising approaches such as decoding the user's auditory attention using brain signals (e.g., O'Sullivan et al. 2015) have emerged.

Previous studies have found that both hearing-impaired and normal-hearing listeners could benefit from vision-guided audio steering in a speech-on-speech masking situation (e.g., Favre-Félix et al. 2018). Nevertheless, these studies utilized traditional eye-tracking systems, which occlude the user's field of vision and are thus not convenient for real-life use. Another eye-gaze tracking technique, electrooculography (EOG), is well known. This technique detects eye-gaze direction by measuring eye potential (electrooculogram) generated by a positive charge in the cornea and a negative charge in the retina, using a plurality of electrodes placed either horizontally or vertically around the eyeballs. Although, EOG has several advantages over traditional eye-gaze tracking methods, such as being independent from outside light, the shape of the eye, or the opening state of the eye, it cannot be embedded in a hearing device as it requires that the electrodes requisite for EOG monitoring be placed around the eyes, making it both uncomfortable and non-ergonomic.

To address this issue, researchers have investigated the usage of in-ear electrooculography to estimate eye gaze for hearing aid steering, showing a significant reduction in listening effort (Favre-Félix et al. 2018). In-ear electrooculography has been shown to yield a limited speech-selection accuracy of around 60% (Favre-Félix et al. 2018). Hence, although in-ear EOG can be used to steer hearing aids to improve speech intelligibility, it is not accurate enough for actual real-life needs (Favre-Félix et al. 2018). One important factor for this low precision is the low signal-to-noise ratio (SNR) due to the few numbers of electrodes placed inside the ear. One way to tackle this problem is to increase the SNR by recording more signals from not only inside the ear, but also around the ear. This approach has a competitive advantage over the method of recording signals from inside the ear and around the eyeballs since an around-ear solution can be worn as a consumer product during daily activities. Although around-ear EEG recordings are possible with recording devices such as cEEGrid (Debener et al. 2015), no research has explored the estimation of eye-gaze using around-ear signals. Practical applications for real-time estimations of eye-gaze in audio steering could be achieved through estimation of the absolute eye-gaze from sensors placed in and around one or both ears.

Although eye-gaze orientation can inform a hearing device about the attention direction of the wearer, the knowledge about gaze orientation in relation to head and trunk orientation can provide the hearing device with some complementary information about the action and intention of the user in the environment, and thus allow delivery of a better listening experience. Some studies have investigated methods that could predict head-rotation movements with respect to trunk orientation using neck electromyogram (EMG) signals (Farshadmanesh et al. 2012). The combination of inertial (accelerometer, gyroscope, and magnetometer) signals to estimate the head rotation while using around-ear EOG and EMG signals could be used to estimate the relative orientation of the gaze direction to the neck and head.

Nevertheless, relying only on the gaze direction and head rotation for audio steering has some limitations. Even with perfect accuracy, these eye gaze and head rotation tracking methods ultimately assume that the user can direct their gaze or head towards the source of interest.

However, many situations require attention to a sound that originates outside of one's visual field, for instance in an adjacent room, or from an unknown location. In such situations, if a device is steered by gaze or head rotation, the target sound cannot be identified, rendering these approaches unnatural, unreliable, and in some cases, such as driving a vehicle, unsafe.

A comprehensive solution that does not rely on physical intervention or visual identification of a target signal does not yet exist for audio steering. For such selective enhancement, current research in auditory attention decoding (AAD) is investigating the use of brain signals to decode an individual's focus of auditory attention (e.g., O'Sullivan et al. 2015). AAD has been investigated using many neuroimaging techniques. The paramount approach for consumer application is electroencephalography (EEG) because it is non-invasive, wearable, cost effective and has the high temporal resolution required (O'Sullivan et al. 2015). In general, AAD has been successfully implemented in research, though none of the existing options have the capability to be adapted to real-time applications. Other limitations to this method for real-life applications include the need for recalibration of the decoders with each slight variation of electrode placement, as well as the requirement of large training datasets (Miran et al. 2018). Thus, researchers are exploring alternative solutions to mitigate the bottleneck need for supervised training data by dynamically updating the decoding models in real-time (Miran et al. 2018). Moreover, in order to implement AAD in a hearing device for real-life applications, the accuracy and speed of attention decoding should be improved using miniaturized EEG systems located around the ear or even within the ear, which can be worn as a consumer product during daily activities. This device could enable the real-time detection of auditory and visual attention using in-ear and around-ear electrode configurations embodied in a hearing assistance device which employs both linear decoding models, as well as non-linear methods, such as artificial neural networks, which are suitable for real-time decoding of the auditory attention with and without having access to isolated speech signals.

In addition to the findings of AAD research that focus on the relationship between speech and brain signals in time domain, neurophysiological experiments have shown that neural oscillations of the brain signal (brain rhythms) are closely associated with sensory processing (Buzsáki and Draguhn, 2004), including sound and speech processing (e.g., Giraud and Poeppel, 2012). To describe different brain functions in processing sensory information, neural oscillations are categorized into five canonical frequency bands: delta, theta, alpha, beta, and gamma oscillations. Noteworthily, it has been shown that during speech perception, the energy envelopes of different frequency bands carry important information about speech content (Shannon et al., 1995). For instance, experimental findings have suggested that synchronization between oscillations of brain networks and the fluctuations in speech signals may help listeners to parse speech into linguistic constituents (e.g., Luo and Poeppel, 2007). Further recent evidence has shown that some brain rhythms, such as low-frequency (delta and theta) bands, show greater speech-EEG entrainment for attended speech compared to ignored speech (Viswanathan et al., 2019). Thus, to enhance the performance of the existing linear and non-linear models of AAD. it is relevant to consider the modulation of cortical entrainment in different frequency bands with relation to the spectrotemporal information of speech sounds.

Additional neuroimaging techniques have been investigated as possible future alternatives to electroencephalography for real-time brain imaging with high temporal and spatial resolution, such as functional near infrared spectroscopy (fNIRS), magnetoencephalography (MEG), optical pumped magnetoencephalography (OP-MEG), giant magnetoimpedance (GMI), and functional ultrasound (fUS). The leading such alternative modality is fNIRS, which measures the hemodynamic response of the brain to a stimulus, due to its advantages: it is non-invasive, quiet, does not interfere with electromagnetic devices (van de Rijt et al., 2018), is less sensitive to movement, has high SNR without the need for conductive gels, and has comparable spatial resolution. Though fNIRS is the most advanced alternative, it is still early in development; but with further efforts, it or other novel modalities may one day reach viability as either a compliment or alternative to EEG in consumer devices and could work in conjunction with sound processing techniques to select sounds of interest based on the attention of a user.

A complete solution to real-time applications of AAD requires these areas of research to be performed synergistically with sound-selection techniques. Though most AAD studies use simplified situations with access to clean speech, a few recent studies have investigated separation of individual signals from audio mixtures in an offline process (Aroudi and Doclo 2019) or in semi-real-time (Han et al. 2019). One proposed real-time solution is beamforming, or the ability to extract sound signals from only a certain direction, which is used successfully in most hearing aids for noise reduction and speech enhancement (Doclo et al. 2010).

A beamformer is a signal-processing technique effectively used in conjunction with multiple microphones, referred to as a microphone array, to extract desired sound signals in noisy environments (Michel 2006). Binaural beamforming not only reduces unwanted sounds, but also preserves the acoustic scene's spatial impression for the listener through preserving the binaural cues of a target sound source (i.e., interaural time and level differences), which allows the tracking of moving speech sources in a reverberant environment (e.g., Doclo et al. 2015). Although these approaches seem to be promising, additional methods have emerged that enhance robustness for real-life noise situations by using external microphones in conjunction with head-mounted microphones (e.g., Göβling, Middelberg, and Doclo 2019). Experimental results of an online implementation of a beamformer, which uses recorded signals of a moving speaker and diffuse noise in a reverberant environment, show considerable improvement in terms of signal to noise ratio (SNR) (Göβling, Middelberg, and Doclo 2019). Overall, the use of external microphones for beamforming is very promising for valuable reasons: i) it improves SNR, ii) it is adaptable to real-life situations involving moving sound sources, and iii) it is widely accessible as built-in omnidirectional microphones in portable consumer devices such as smartphones, smart glasses, virtual or augmented reality headsets, smart watches. or other consumer devices.

Although beamforming techniques seem successful at sound selection, they are beneficial only when there is enough spatial separation between target and interfering speakers. An alternative and possibly complementary method is to leverage the recent successes in automatic-speech separation algorithms with deep neural network (DNN) models (Chen, Luo, and Mesgarani 2016; Luo, Chen, and Mesgarani 2018). Furthermore, it has been claimed that neural network approaches could automatically separate unseen sound sources in real-time applications only using input from a single microphone (e.g., Han et al. 2019; Mobin and Olshausen 2019). However, these approaches have only been tested in laboratory settings and with few speakers (e.g., Han et al. 2019; Mobin and Olshausen 2019). More validation is needed before using these techniques for separation of multiple sound sources in different acoustic environments (e.g., bus vs. classroom). To improve the ability of sound source separation for dynamic situations, instead of a single channel input, the input to a deep neural network can be taken from the binaural multichannel signals with the addition of external microphones, which allows the separated sound sources to carry additional spatial information. Overall, though both beamforming and neural network approaches have opened the door to more robust sound selection methods, no existing solutions perform one primary function: the effortless selection of a single sound of interest amongst several sounds with natural sound quality (e.g., Han et al. 2019; Mobin and Olshausen 2019). Thus, the solution should provide a speech separation and enhancement system that comprises the combination of binaural beamforming and deep learning using microphone arrays comprising directional and omnidirectional microphones on each pair of a hearing device in addition to an input from external microphones in order to improve the quality and reliability of speech enhancement using both beamforming and neural network approaches.

To summarize, there are new promising advances in addressing the very significant disabilities of hearing impairment in noisy environments. Advances have been achieved through isolated research in both interpreting attentional cues from brain signals and in environmental sound processing, including beamforming and machine learning-assisted sound separation. There is a lack of a comprehensive, robust, and industrially feasible hearing device that inputs signals recorded non-invasively from around the ear and ear canal of the users as i) electroencephalogram (EEG) signals, ii) electromyogram (EMG) signals, iii) electrooculogram (EOG) signals, iv) inertial signals collected from accelerometer, gyroscope, and magnetometer, v) other biosignals, vi) sounds played through their devices, vii) environment sounds recorded using microphone arrays including inputs from directional and omnidirectional microphones on each pair of the hearing device and at least one microphone in a portable-consumer device such as smartphones and smartwatches, viii) additional environmental signals that can be collected from electronic devices, vehicles, distributed networks, home systems, automotive systems, and other sensor systems; and then outputs i) the probability of the users paying attention to auditory and visual stimuli, ii) separated sound sources, iii) head direction of the user, iv) eye gaze direction of the user, and v) neck orientation of the user, vi) gaze-head-trunk relative orientation of the user.

SUMMARY OF THE DESCRIPTION

In one aspect, there is provided a hearing assistance device comprising a body configured to engage a user's ear, at least one ear sensor mounted to the body for collecting electroencephalogram and/or electrooculogram and/or electromyogram signals, at least one microphone for collecting environmental auditory signals; and a processor configured to use the electroencephalogram and/or electrooculogram and/or electromyogram signals and with or without auditory signals as input to linear or non-linear neural network algorithms to determine auditory attention of the user in real time.

In a further aspect, the at least one ear sensor comprises one or more in-ear sensors and/or one or more around-ear sensors.

In a further aspect, the hearing devices comprise at least one microphone mounted to the body of the hearing device and/or at least one external microphone with or without relying on the neural signals collected from electroencephalogram readings to apply sound-separation processing to the mixed sound signal from the various environmental sound sources to derive a plurality of separated sounds.

In a further aspect, at least one microphone comprises a single microphone or a microphone array of a plurality of microphones.

In a further aspect, the array of a plurality of microphones comprises directional and omnidirectional microphones mounted to the body.

In a further aspect, the microphone array further includes external microphones.

In a further aspect, the external microphone source is part of a cell phone, and/or smart watch, and/or smart glasses, and/or other electronic device for collecting sounds.

In a further aspect, the electroencephalogram and/or electrooculogram and/or electromyogram signals are collected from sensors in both the right ear and left ear of a user and the signals from the right ear and signals from the left ear are used as inputs into linear and/or non-linear models to detect the eye gaze of the user.

In a further aspect, the hearing devices comprises a head orientation sensor for determining the relative orientation between the eye gaze, head, and trunk.

In a further aspect, the head orientation sensor is a combination of one or more of an accelerometer, and/or gyroscope, and/or magnetometer.

In a further aspect, the hearing device system comprises the hearing device connected through wireless transmission with other sensors from an external electronic device to provide additional information concerning the state and/or the environment of the user.

In a further aspect, a hearing assistance device is taught comprising: a body configured to engage a user's ear; at least one ear sensor mounted to said body for obtaining at least one biosignal indicative of the user's attention; at least one microphone for collecting at least one environmental auditory signal; and a processing unit adapted to process said at least one environmental auditory signal to determine a plurality of separated sound signals corresponding to multiple sound sources in an environment. The processing unit can be further adapted to use the at least one biosignal to determine which of the plurality of separated sound signals to which the user is attentive in real-time.

In a further aspect, the signals can be integrated with signals from an electronic device or system to provide a comprehensive understanding of the user and their environment; said integration being performed using a sensor fusion method, such as Kalman filter.

In a further aspect, the at least one biosignal is chosen from the group consisting of electroencephalogram (EEG), electrooculogram (EOG), electromyogram (EMG), accelerometer, gyroscope, and/or magnetometer signals.

In a further aspect, the at least one biosignal is used to determine, in real time, at least one of auditory attention of the user, visual attentional direction of the user and physical orientations of the user's head, gaze, and trunk.

In a further aspect, the at least one ear sensor comprises at least one in-ear sensor and/or around-ear sensor used to obtain the at least one biosignal chosen from the group consisting of EEG, EOG and EMG.

In a further aspect, obtaining one or more of the EEG, EOG and/or EMG signals of the user comprises: obtaining a change in electrical potential of the user via a non-invasive recording from at least one ear sensor comprising a combination of one or more in-ear sensors and/or around-ear sensors.

In a further aspect, the at least one microphone comprises an array of microphones.

In a further aspect, the array of microphones comprises directional and/or omnidirectional microphones mounted to the body of the device.

In a further aspect, the microphone array further includes an external microphone.

In a further aspect, the external microphone source is located on a portable consumer device such as smartphones, smart glasses, virtual or augmented reality headsets, smart watches, or other consumer devices.

In a further aspect, the sound processing and/or separation step is performed by a combination of one or more of the left and right bodies of the device.

In a further aspect, the processed and/or separated sounds can be combined to increase the performance of sound processing of both left and right sides.

In a further aspect, the at least one biosignal is an EEG signal, and the EEG signal is used as input into linear and/or non-linear models to determine the auditory attention of the user and/or separate sound signals from the mixed sound signal.

In a further aspect, the EEG are band pass filtered and/or feature extracted with said processing unit, then used to establish a measurement of the user's neural oscillations of delta, theta, alpha, beta and/or gamma activity.

In a further aspect, linear and/or non-linear models are applied to the at least one environmental auditory signal to identify the plurality of separated sound signals corresponding to multiple sound sources in an environment.

In a further aspect, the linear and/or non-linear models are shallow or deep neural network algorithms.

In a further aspect, the linear and/or non-linear models are coupled with beamforming-based speech enhancement techniques to the mixed sound signal from the multiple sound sources to derive a plurality of separated signals In a further aspect, the at least one biosignal is collected from sensors in or around both the right ear and left ear of a user and the signals from the right ear and/or signals from the left ear are used as input into linear and/or non-linear models to identify eye gaze.

In a further aspect, the device can be configured to provide an EOG signal from in and/or around the ear representative of eye gaze is determined based on the left and right amplified voltages $V_{left}$ and $V_{right}$.

In a further aspect, the device can be configured to provide that the EOG signal is a function (f) of one or more or an average of multiple signals from the left amplified voltages $V_{left}$, $EOG=f(V_{left})$, or right amplified voltages $V_{right}$, $EOG=f(V_{right})$ or from the difference between one or more or an average of multiple signals of the left and right amplified voltages $V_{left}$ and $V_{right}$, $EOG=f(V_{left}-V_{right})$.

In a further aspect, the device can comprise a processing unit configured to provide an EOG control signal for controlling a function of said at least one hearing device based on said EOG signals.

In a further aspect, linear and/or non-linear models are applied to identify the horizontal and vertical movement of the user's eye and provide gaze angles in a fixed coordinate system.

In a further aspect, the linear and/or non-linear models use linear and non-linear activation functions respectively embedded in a shallow or deep neural network algorithm.

In a further aspect, at least one of the hearing devices comprises a beamformer unit, and wherein said at least one hearing device is configured to steer the beamformer angle of maximum sensitivity towards the gaze direction.

In a further aspect, the device can provide absolute coordinates of a sound source to identify individual attended sound signals from the plurality of sound signals.

In a further aspect, the device can further comprise a processing unit configured to provide a control signal to direct sound processing based on a computed head rotation angles of the user in a fixed coordinate system using said linear and/or non-linear models.

In a further aspect, the device can further comprise EMG in-ear and/or around-ear sensors for determining neck orientation angles of the user relative to the trunk in a fixed coordinate system.

In a further aspect, a signal processing unit integrates the horizontal and vertical angle of the user's gaze derived from EOG signals with the angle of head rotation computed using accelerometer, gyroscope, and magnetometer signals, and the angle of neck orientation relative to the trunk is estimated using EMG signals to compute the gaze-head-neck relative orientation angles in a fixed coordinate system.

In a further aspect, two hearing devices are provided wherein at least one of the hearing devices comprises a beamformer unit, and wherein said at least one hearing device is configured to steer the beamformer angle of maximum sensitivity towards the optimized direction.

In a further aspect, a plurality of hearing devices are provided wherein at least one of the hearing devices comprises a beamformer unit, and wherein said at least one hearing device is configured to steer the beamformer angle of maximum sensitivity towards the optimized direction.

In a further aspect, the device can comprise providing absolute coordinates of a sound source to identify individual attended sound signals from the plurality of sound signals.

In a further aspect, there is provided a method for identifying a sound which is the subject of a user's attention comprising measuring at least one biosignal of the user; collecting at least one environmental auditory signal; performing sound-separation process on the at least one environmental auditory signal to identify a plurality of separated sound signals corresponding to different environmental sounds; using the at least one biosignal to determine which of the plurality of separated sound signals to which the user is attentive.

In a further aspect, the at least one measured biosignal is chosen from the group consisting of one or more of electroencephalogram (EEG), electrooculogram (EOG), electromyogram (EMG), accelerometer, gyroscope, and magnetometer signals., In a further aspect, the at least one biosignal is measured using sensors in and/or around the ear.

In a further aspect, the at least one biosignal is used to determine, in real time, at least one of auditory attention of the user, visual attentional direction of the user and physical orientations of the user's head, gaze, and trunk.

In a further aspect, the method may comprise: processing the selected at least one of the plurality of separated sound signals based on the selected sound source derived from the said auditory attention identification method, including performing one or more of: amplifying the selected one or more of the plurality of separated signals, or suppressing at least one of the non-selected sound signals from the sounds signals.

In a further aspect, applying the sound-separation processing to the mixed sound signal from the multiple of sound sources to derive the plurality of separated signals comprises: applying neural-network-based speech-separation processing to the mixed sound signal from the multiple of sound sources to derive the plurality of separated signals.

In a further aspect, the neural-network-based sound-separation processing is applied to the mixed sound signal from the multiple sound sources in isolation or in combination with at least one EEG signal recorded from either the left and/or right ear.

In a further aspect, applying beamforming-based sound-selection processing to the mixed sound signal from the multiple sound sources comprises: providing the mixed sound signal from the multiple sound sources to a beamformer configured to identify individual sound sources from the mixed sound signal.

In a further aspect, the at least one biosignal is an average of multiple of the EOG signals collected from the left and right sides of the body which results in amplified voltages $V_{left}$ and $V_{right}$ are used after being band pass filtered and/or feature extracted with said measuring device or system, establishing a measurement of the signal mean, standard deviation, slope, average velocity, maximum velocity, average acceleration, peak-to-peak amplitude, maximum amplitude, and/or time-to-peak.

In a further aspect, processing the selected one or more of the plurality of separated sound signals, including performing one or more of: amplifying the selected one or more of the plurality of extracted beamformed signals in direction of attended sound sources, or attenuating at least one non-selected signal from the plurality of signals.

In a further aspect, the device can receive through transmission additional signals from external electronic devices to understand the conditions of the state and attention of the user and the environment.

In a further aspect, the signals can be integrated with signals from an electronic device or system to provide a comprehensive understanding of the user and their environment; said integration being performed using a sensor fusion method for integrating a combination of said auditory attention data, gaze direction data, gaze-head-trunk orientation data, location data, sound data, separated sounds, raw EEG, EOG, and/or EMG signals, and inertial data, and/or signals from external electronic devices that provide additional information concerning the environment of the user, such as visual data, etc. to identify and provide the focus of attention of the user and perform other attention-related tasks.

In a further aspect, the sensor fusion method can be used to furthermore improve the data, e.g., to reduce drift, increase robustness, and denoise speech signals, EOG signals, or other signals.

In a further aspect, the device includes other biopotential sensing modalities, including one or more of functional near infrared spectroscopy (fNIRS), magnetoencephalography (MEG), optical pumped magnetoencephalography (OP-MEG), giant magnetoimpedance (GMI), and functional ultrasound (fUS), wherein the processing unit is adapted to process one or more of fNIRS, MEG, OP-MEG, GMI, fUS, EEG, EOG, EMG, accelerometer, gyroscope, and magnetometer signals and auditory signals to: determine in real time auditory attention of the user; determine the visual attentional direction of the user; determine physical orientations of the user's head, gaze, and trunk; the device to obtain one or more of fNIRS, MEG, OP-MEG, GMI, fUS, EEG, EOG, EMG, accelerometer, gyroscope, and magnetometer signals of the user indicative of the attention of the user.

BRIEF DESCRIPTION OF THE FIGURES

Embodiments will now be described by way of example only with reference to the appended drawings wherein.

DETAILED DESCRIPTION

The terms "comprise", "comprises", "comprised" or "comprising" may be used in the present description. As used herein (including the specification and/or the claims), these terms are to be interpreted as specifying the presence of the stated features, integers, steps, or components, but not as precluding the presence of one or more other feature, integer, step, component, or a group thereof as would be apparent to persons having ordinary skill in the relevant art. Thus, the term "comprising" as used in this specification means "consisting at least in part of. When interpreting statements in this specification that include that term, the features, prefaced by that term in each statement, all need to be present but other features can also be present. Related terms such as "comprise" and "comprised" are to be interpreted in the same manner.

Unless stated otherwise herein, the article "a" when used to identify any element is not intended to constitute a limitation of just one and will, instead, be understood to mean "at least one" or "one or more".

The following relates to multimodal-hearing devices and systems that use signal processing methods and machine learning approaches such as artificial neural networks to achieve a combination of i) interpreting the auditory attention of the user, ii) interpreting the visual attentional direction of the user, iii) inferring physical orientations of the user's head, gaze, and trunk, as well as iv) performing sound-source separation, and v) speech enhancement which are all done by employing the user's brain signals and other biosignals in conjunction with information gathered from the environment, including auditory data and data from other sensors providing relevant information on the environment of the user.

Figure 1:
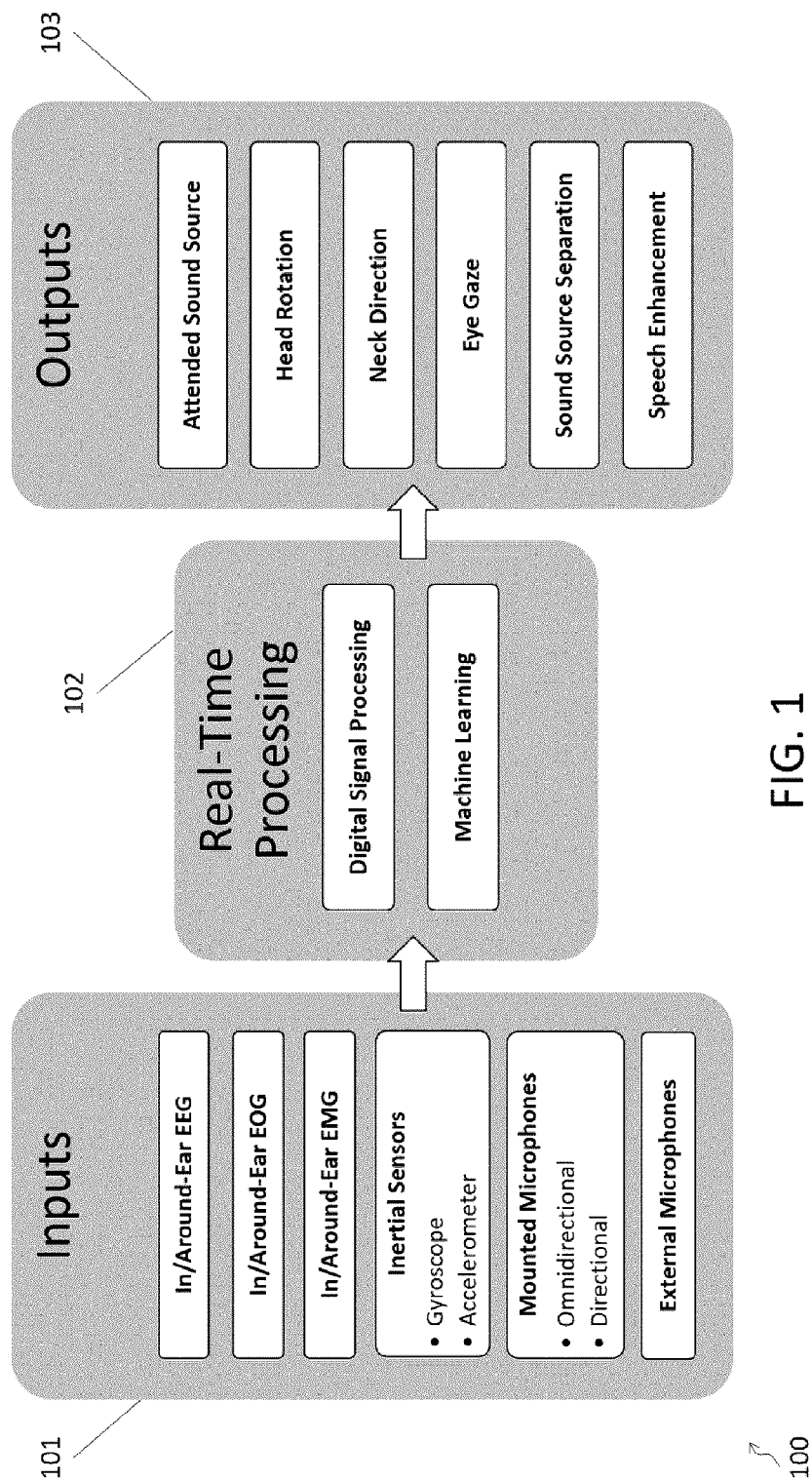
FIG. 1 is a block diagram of the input 101, output 103 and processing unit 102 of the hearing assistance device, according to one embodiment of the present subject matter.
Figure 3:
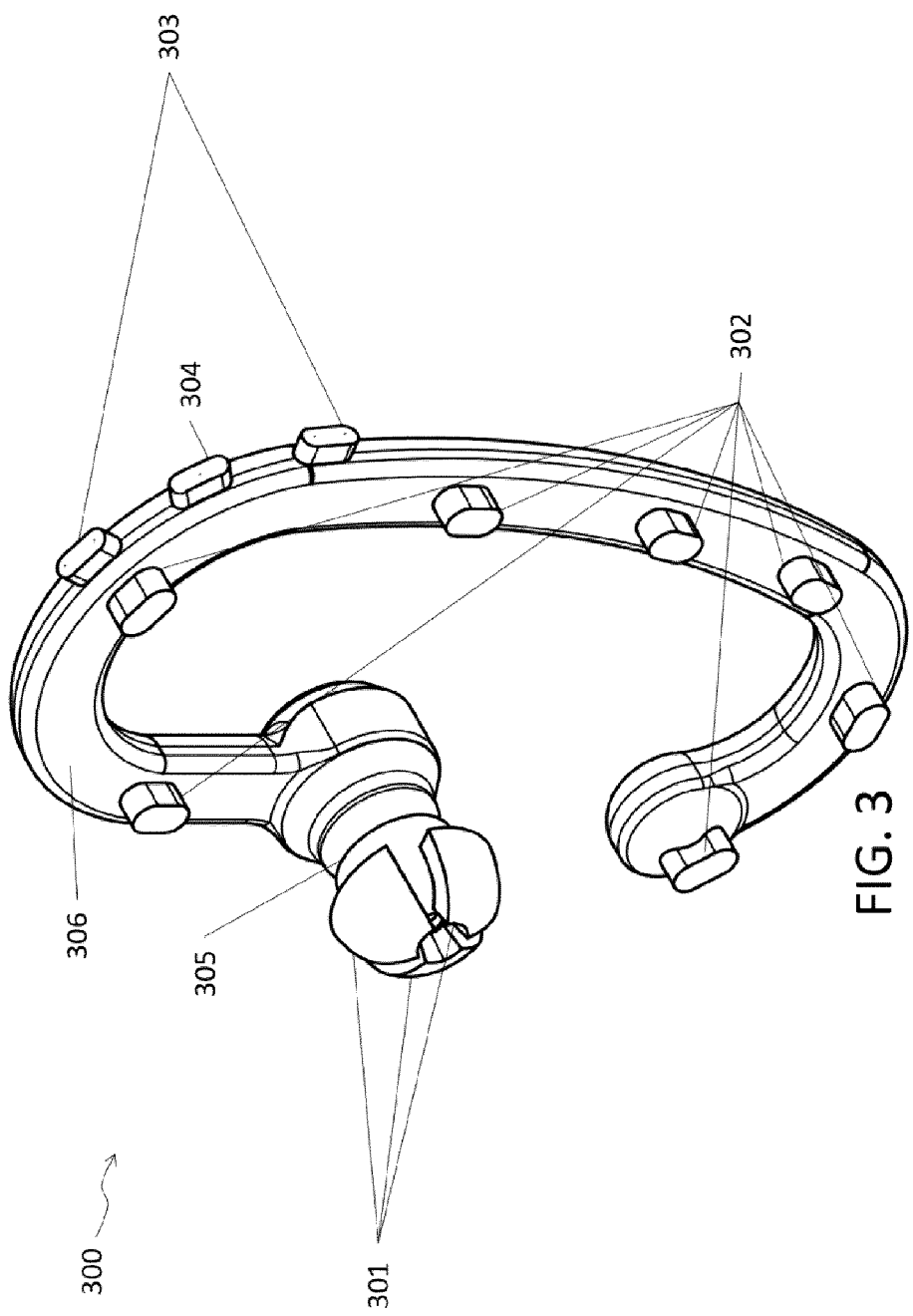
FIG. 3 depicts a schematic illustration of a single hearing assistance device 300 including in-ear electrodes 301, around-ear electrodes 302, and both omnidirectional 304 and directional 303 microphones. The in-ear and around-ear electrodes collect EEG, EOG, and EMG data from the user.

FIG. 1 is a block diagram of a system 100, the outputs 103 of which can be used for a variety of different applications. In one embodiment, a hearing device 300, shown in FIG. 3 is provided as a mounting device for all the sensors or inputs 101. The signals from these sensors are used as input into a processor for real-time processing 102 including, at least signal processing and machine learning algorithms. Depending on which inputs 101 and algorithms are used, a variety of outputs 103 are possible. These outputs 103 could include, but are not limited to, attended sound source, head rotation, neck direction, eye gaze, sound source separation, and speech enhancement.

An embodiment wherein a multimodal hearing assistance device 201 is configured to collect the input signals will be discussed below. Furthermore, each output will be discussed individually.

Multimodal Hearing Assistance Device

With sound amplification provided by current hearing aids, users report difficulty in understanding hearable speech (Shield 2006); or speech that they do understand requires great effort (Pichora-Fuller et al. 2016). This is because hearing assistance devices are extremely limited in their ability to mimic the complex audio processing of the brain, such as the capability to listen to a single sound among many sounds, track a moving speaker, and switch attention between sounds of interest (Hougaard and Ruf 2011; Sim and Kim 2019). The device 300, shown in FIG. 3 enhances a desired signal and suppresses distracting noises by relying on the attention of a user. The attention of the user is determined from a plurality of sensors. In a preferred embodiment of the device 300, a plurality of different measurement devices are incorporated into the device, including one or a plurality of in-ear sensors 301, one or a plurality of around-ear 302 versatile dry electrodes, and one or more microphones or microphone arrays preferably consisting of directional 303 and omnidirectional 304 microphones. Furthermore, accelerometer, and/or gyroscope, and/ or magnetometer sensors may also be included.

The in-ear sensors and around-ear sensors are preferably made of conductive material, including, but not limited to, metals or polymers with the ability to measure bioelectric signals of the user with whom they have contact. These sensors could be capable of measuring at least one of a variety of signals, including signals such as electroencephalogram (EEG), electromyogram (EMG), and electrooculogram (EOG) signals. In the example embodiment shown, 3 in-ear sensors 301 are located at the end of an extension support 305 that extends inwardly from the body 306 of the hearing device 300. When in use, the in-ear sensors 301 are preferably electrodes, and engage the ear canal of the user's ear. In a preferred embodiment, there could be one or multiple in-ear sensors as could be appreciated by a person skilled in the art. Said in-ear and around-ear sensors may also be in the form of other brain imaging modalities, such as used for functional near infrared spectroscopy (fNIRS), magnetoencephalography (MEG), optical pumped magnetoencephalography (OP-MEG), giant magnetoimpedance (GMI), and functional ultrasound (fUS), which can detect the brain's response to sound stimuli, as can be appreciated by a person skilled in the art.

The body 306 of the device 300, further includes a plurality of around ear sensors 302. These sensors are preferably mounted on a back surface of the body 306 in such a fashion that they contact the user's head. In a preferred embodiment shown, there are 7 around ear sensors, a person skilled in the art would understand that the number of around ear sensors could vary.

Figure 2:
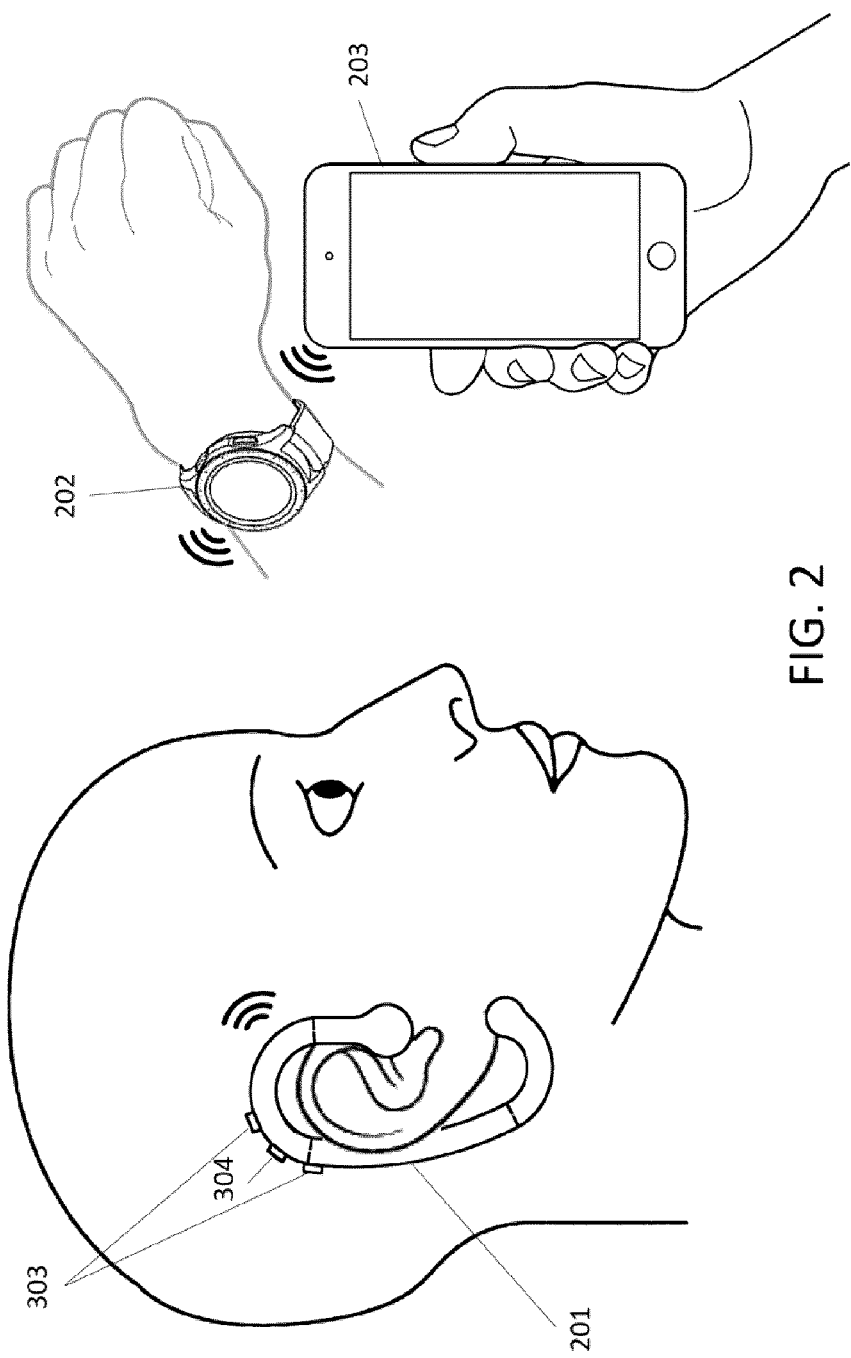
FIG. 2 depicts a schematic illustration of an embodiment of a hearing assistance device 201 and its integration with a smartphone 203 and a smartwatch 202.

The microphone arrays consist of directional microphones 303 and omnidirectional microphones 304 located along the body 306 of the device 300. These microphones collect audio information from the environment. The directional microphones are preferably placed at equal distances from the omnidirectional microphone. In the embodiment shown, two directional microphones and one omnidirectional microphone are mounted to the top surface of the body 306. As can be seen in FIG. 2, in a preferred embodiment, the microphones are located on the body 306 at a position corresponding to the top rear portion of the user's ear. Although three microphones are shown in the figures, it would be appreciated by a person skilled in the art that the number of microphones used could be varied.

Using signal processing methods and machine learning approaches previously limited by computation time, a delay in data transmission, and lack of appropriate sensors, the device understands the selective visual and auditory attention of the user using information such as brain signals, eye gaze, and head and neck orientation in order to enhance the desired sounds through isolating sounds using techniques in sound-source separation and beamforming methods. Visual attention is used as it provides information about the direction and importance of direction of the focus of attention; whereas auditory attention provides information about qualities of the attended audio signal. These in conjunction with machine learning techniques herein explained, allow the device to understand the focus and conditions of the signal of attention and allow the device to personalize the hearing experience for the individual through enhancing the desired and attended sounds while suppressing distracting noise.

Real-Time Tracking of Auditory Attention from EEG Using In- and Around-Ear Electrodes The current state-of-the-art techniques for detecting selective auditory attention use linear models, which are not able to classify attention within a short time interval and thus are not well-suited for real-time applications such as smart hearing devices or brain-computer interface systems (Miran et al. 2018). Along with these linear models, nonlinear approaches could be used based on deep neural networks to exploit the power and biological relevance of nonlinear processing, which represents a rich source of possibilities. The motivation for applying deep artificial neural networks to the attention-decoding problem is that non-linear decoders provide improved performance relative to linear decoders due to their ability to parallel the brain's inherent non-linear processing of perceptual stimuli such as sounds. To this end, two non-linear neural network approaches are employed as in FIG. 1, one which reconstructs the stimuli and uses the correlation-based classifier to decode the attentional focus of the user using a method that is optimized for real-time application, and the other which uses an end-to-end classification network which makes a direct similarity prediction between the EEG and each stimulus while reducing the computation load on the device without access to sound signals. Deep neural network methods include WaveNet (Tamamori et al. 2017), three-dimensional convolutional neural networks, and artificial recurrent neural network (RNN) architectures such as Bidirectional Long Short-Term Memory (BLSTM) neural networks.

Real-Time Visual Attention Decoding Via Eye Gaze Tracking Using In- and Around-Ear Electrodes Current eye gaze tracking methods based on an electrooculogram either use signals recorded from around the eyes or a limited number of signals inside the ear. The system described herein detects a gaze direction of a user based on electrooculogram and electromyogram signals recorded from the in-ear sensors 301 and around-ear sensors 302. The additional signals from the around-ear sensors 302 lead to an increase in signal quality and thus enhances the accuracy and resolution of eye gaze detection. The horizontal and vertical gaze direction (right, left, up, down and center) as well as the angle of the gaze relative to the head is computed based on approximations of voltage ratios and/or subtraction or other interactions between and within the right and left in-ear sensors 301 and around-ear sensors 302. By using sensors located on both the left ear and right ear of the user, the signal quality of the electrooculography can be increased by subtracting the signals from one another in order to remove distortions that appear as common artefacts between the signals which represents unwanted signal noise. The extraction of horizontal and vertical direction and gaze angles is decoded using thresholding methods as well as linear and non-linear models, including but not limited to. Linear and Logistic Regressions, Naive Bayes, Support Vector Machine, K-nearest Neighbors, Decision Tree and Random Forest and Neural Network models such as convolutional neural networks, and from these signals, additional information such as electromyography, can be gathered, which is used to determine head rotation and trunk orientation, providing an understanding of the absolute gaze direction in the user's field, and thus the sensors behind the ear provide additional information about the state of the user. Another advantage of estimating gaze direction from a location behind the ear is that the movement from the eye affects movement of the eardrum, and the electrodes placed around the ear are sensitive to this resulting muscular activity. This leads to increased accuracy in the estimation of gaze direction when compared to known methods.

Gaze-Head-Trunk Relative Orientation

Previous attempts showing the utilization of eye gaze to direct audio steering have not included the effects of head movements and head orientation relative to trunk orientation. To perform audio steering using eye gaze for real-time estimations, the behavior and posture of the users using the relative orientation between eye gaze, head, and trunk is first determined. The eye gaze estimation is computed using the previously mentioned method. Using signal processing and machine learning approaches, the head rotation is computed using a combination of one or more of accelerometer, gyroscope, and magnetometer signals, and the neck orientation relative to the trunk is estimated using in-ear 301 and around-ear 302 EMG signals. Finally, all this information is integrated to compute the gaze-head-neck relative orientation.

Speech and Sound Enhancement Using Microphone Arrays Including External Microphones Current speech enhancement and sound source separation methods either use inputs 101 from single microphone or binaural multichannel signals mounted on the hearing device. In the example shown in the figures, sound separation and enhancement are done through implementing binaural beamforming and deep neural network approaches using signals recorded from binaural on-device microphones 201 in conjunction with one or more external microphones on smartphones 203 or watches 202 or other electronic devices for collecting audio signals (FIG. 2). This allows the separated sound sources not only to have higher signal-to-noise ratios, but also carry additional spatial information about the origin of the sound sources. The external devices such as smartphones 203 and/or smartwatches 202 and/or other electronic devices for collecting audio signals could be used to process all or a subset of the information gathered from the sensors of the hearing device (FIG. 3). The hearing device may further include a method to filter information from said sensors, comprising a sensor fusion method for filtering said location data, and/or said electroencephalogram and/or electrooculogram and/or electromyogram signal(s), and/or said combined location data, and providing auditory attention information, eye gaze angles or directions, or gaze-head-trunk orientations in a fixed coordinate system.

Speech and Sound Enhancement Using Microphone Arrays Including External Microphones Current speech enhancement and sound-source separation methods either use inputs 101 from a single microphone or binaural multichannel signals mounted on the hearing device. In the preferred embodiment shown in the figures, sound separation and enhancement are done through implementing binaural beamforming and deep neural network approaches using signals recorded from binaural on-device microphones 201 in conjunction with one or more external microphones. In the preferred embodiment, shown in FIG. 2, the binaural on-device microphones comprise two directional microphones 303 and one omnidirectional microphone 304, although other arrangements would be known to a person skilled in the art. The external microphones could be mounted in a variety of different ways, for example, a microphone could be mounted on a band for fixing around the wrist of the person or could be contained in a separate device for carrying. It is also possible to utilize the microphones available in many smart devices that a user may already own. For example, the microphone on a smartphone 203 or smartwatch 202 could be used. It can be appreciated that other devices with the ability to remotely connect to the hearing device 300 could also be used. This preferred embodiment, which uses the smartphone 203 and smartwatch 202, allows the separated sound sources not only to have higher signal-to-noise ratios, but also to carry additional spatial information about the origin of the sound sources.

Attention Tracking Based on Sensor Fusion Models

Sensor fusion models are algorithms that combine series of noisy data in order to produce estimates of unknown variables. By estimating a probability distribution based on these combined data, these estimates tend to be more accurate than those based on a single measurement alone. One example of these is the Kalman filter suited for temporal applications, where the probability distributions based on the data is segmented by time for real-life applications. By implementing the sensor fusion model into the hearing device, in addition to integrating the data from all the sensors of the device, the system can be modified to include the information from sensors external to those provided on the hearing device itself, including information from sensors that provide additional knowledge of the environment of the user, such as visual, or other sensory information. These can be combined with the information of the user and the user's attention provided from the hearing device in a signal fusion method for filtering a combination of one or more of said auditory attention data, gaze direction data, gaze-head-trunk orientation data, location data, sound data, separated sounds, raw EEG, EOG, EMG signal(s), and/or said combined location data, in conjunction with one or more of these external signals from external electronic devices that provide additional information concerning the environment of the user. This fusion of multiple on-device and off-device sensors can be used to provide a holistic understanding of the environment and state of the user, identify the user's attention, and perform sound separation. Furthermore, these data may be further improved by the use of sensor fusion methods, e.g., to reduce drift (e.g. [Manabe & Fukamoto; 2010]), increase robustness, and denoise speech signals or other signals.

Alternative Embodiments

The above-described principles can be modified according to the following: the device can be miniaturized into a smaller package such as an in-ear hearing device, or the device can be enlarged to be suitable for a headphone, glasses frame, virtual or augmented reality headset, or helmet unit.

The smaller package resides in an embodiment of an in-ear hearing device that includes: one or more in-ear dry electrodes for the collection of EEG, EOG, and EMG data from the ear canal of the user, omnidirectional and directional microphones placed on an outward face of the body of the hearable device, as well as accelerometer, gyroscope, and magnetometer sensors embedded in the device. Additional miniaturized in-ear dry electrode layers can be added into the device along additional planes of skin contact in the ear to increase the signal-to-noise ratio of the collected signals while maintaining the same effective areas as the inserted earphones.

The larger package resides in an embodiment of a stand-alone headphone unit, glasses frame, virtual or augmented reality headset, or a headphone unit that is incorporated into a helmet including the following elements: around-ear electrodes to be placed in or around the ear of the user that collect EEG, EOG, and EMG data, multiple dry electrodes on the inside of the unit against the skin of the user to collect signals from the scalp, omnidirectional and directional microphones placed both on the outer surface of the unit and/or mounted on the body of a consumer electronic device such as smartphones, smart glasses, virtual or augmented reality headsets, smart watches, or other consumer devices, as well as accelerometer, gyroscope, and magnetometer sensors embedded in the device.

The principles, devices, and systems described herein have applications in many areas that involve detecting the visual and auditory attention of the user, direction of gaze, head, and trunk orientation of the user, as well as spatial sound capture, speech enhancement, sound-source separation, and environment discernment. An advantage this device brings over alternatives is that it can detect the behavior and attention of the user and separate sounds coming from multiple directions (or track moving sound sources) all in a single package by employing several EEG, EOG, EMG dry electrodes, accelerometer, gyroscope, and magnetometer sensors, directional and omnidirectional microphones and additional external microphones in wirelessly-connected portable consumer devices including but not limited to smartphones, tablets, smart glasses frames, virtual or augmented reality headsets, smartwatches, and helmets.

Additional applications include but are not limited to Automotive and heavy machinery and Augmented reality (AR) or virtual reality (VR), each of which is discussed below.

Automotive and Heavy Machinery

Using the principles described above, information on the state of a driver can be interpreted, including, but not limited to, driver's or operator's attention, distraction, fatigue, and mental and physical safety level.

Using the gaze-head-trunk relative orientation and the estimation of the user's gaze, a driver's or operator's eye gaze can be tracked both during the day and night independently of lighting conditions or information provided by any eye-tracking camera.

Using auditory attention decoding methods, the level of attention of a driver or operator to different sounds heard from within the vehicle or machine or in their listening device can be detected.

Using the information about the attended sounds and the gaze of a driver or operator, audio cues that are being heard or ignored can be identified, and similarly visual cues that are being noticed or missed can be identified.

Additional information on the state of the vehicle or environment collected by the sensors of the vehicle or system can be fused with the information on the state of the driver or operator to provide a more holistic understanding of the driving conditions or environment for further safety or attention applications.

Using the EEG, EOG, EMG signals recorded from in-ear electrodes 301 and around-ear electrodes, 302 shown in FIG. 3, the fatigue level of the driver can be predicted from monitoring both the eye conditions and mental conditions of a driver or operator.

All the points described above contribute to the understanding of the level of driver's or operator's attention to the road conditions.

Augmented Reality (AR) or Virtual Reality (VR)

Using the principles described above, information about the user of VR/AR is interpreted, including, but not limited to, the user's attention to visual and auditory stimuli in their virtual environment and the user's head and eye movements and their orientation with respect to the trunk.

Using the gaze-head-trunk relative orientation and real-time visual attention, the AR/VR display can be manipulated to adapt the point-of-view or foveated quality of the scenery.

Using real-time tracking of auditory attention, the level of attention of the user to different sounds in their virtual environment can be detected. Using this information, users can choose what sounds in the environment to enhance and which to attenuate.

Using the information about the attended sounds and the gaze of the AR/VR user, sounds that are being heard or ignored and visual information that is noticed or missed can be identified. This information could be used to create a more immersive, responsive, and natural AR/VR experience.

Although the above description includes reference to certain specific embodiments, various modifications thereof will be apparent to those skilled in the art. Any examples provided herein are included solely for the purpose of illustration and are not intended to be limiting in any way.

Any drawings provided herein are solely for the purpose of illustrating various aspects of the description and are not intended to be drawn to scale or to be limiting in any way. The scope of the claims appended hereto should not be limited by the preferred embodiments set forth in the above description but should be given the broadest interpretation consistent with the present specification as a whole. The disclosures of all prior art recited herein are incorporated herein by reference in their entirety.

REFERENCES

Aroudi, Ali, and Simon Doclo. 2019. "Cognitive-Driven Binaural LCMV Beamformer Using EEG-Based Auditory Attention Decoding." In *ICASSP. IEEE International Conference on Acoustics, Speech and Signal Processing—Proceedings*, Institute of Electrical and Electronics Engineers Inc., 406-10.

Burns, Thomas Howard. 2015. "(12) United States Patent." 2(12).

Chen, Zhuo, Yi Luo, and Nima Mesgarani. 2016. "Deep Attractor Network for Single-Microphone Speaker Separation." http://arxiv.org/abs/1611.08930 (Nov. 27, 2019).

Debener, Stefan, Reiner Emkes, Maarten De Vos, and Martin Bleichner. 2015. "Unobtrusive Ambulatory EEG Using a Smartphone and Flexible Printed Electrodes around the Ear." *Scientific Reports* 5.

Doclo, Simon, Sharon Gannot, Marc Moonen, and Ann Spriet. 2010. "Acoustic Beamforming for Hearing Aid Applications." In *Handbook on Array Processing and Sensor Networks*, Hoboken, NJ, USA: John Wiley & Sons, Inc., 269-302. http://doi.wiley.com/10.1002/9780470487068.ch9 (Nov. 27, 2019).

Doclo, Simon, Walter Kellermann, Shoji Makino, and Sven Erik Nordholm. 2015. "Multichannel Signal Enhancement Algorithms for Assisted Listening Devices: Exploiting Spatial Diversity Using Multiple Microphones." *IEEE Signal Processing Magazine* 32(2): 18-30.

Farshadmanesh, Farshad et al. 2012. "Cross-Validated Models of the Relationships between Neck Muscle Electromyography and Three-Dimensional Head Kinematics during Gaze Behavior." *Journal of Neurophysiology* 107 (2): 573-90.

Favre-Félix, Antoine et al. 2018. "Improving Speech Intelligibility by Hearing Aid Eye-Gaze Steering: Conditions with Head Fixated in a Multitalker Environment." *Trends in Hearing* 22.

Göβling, Nico, Wiebke Middelberg, and Simon Doclo. 2019. "RTF-Steered Binaural MVDR Beamforming Incorporating Multiple External Microphones." http://arxiv.org/abs/1908.04848 (Nov. 27, 2019).

Han, Cong et al. 2019. "Speaker-Independent Auditory Attention Decoding without Access to Clean Speech Sources." Science Advances 5(5), http://advances.sciencemag.org/(Nov. 27, 2019).

Hart, Jamie et al. 2009. "The Attentive Hearing Aid: Eye Selection of Auditory Sources for Hearing Impaired Users." In *Lecture Notes in Computer Science (Including Subseries Lecture Notes in Artificial Intelligence and Lecture Notes in Bioinformatics)*, 19-35.

Hougaard, Søren, and Stefan Ruf. 2011. "EuroTrak I: A Consumer Survey About Hearing Aids." *Hearing Review* 18(2): 12-28, http://www.hearingreview.com/2011/02/eurotrak-i-a-consumer-survey-about-hearing-aids-in-germany-france-and-the-uk/(Nov. 27, 2019).

Kidd, Gerald et al. 2013. "Design and Preliminary Testing of a Visually Guided Hearing Aid." *The Journal of the Acoustical Society of America* 133(3): EL202-7.

Kidd, Gerald. 2017. "Enhancing Auditory Selective Attention Using a Visually Guided Hearing Aid." *Journal of Speech, Language, and Hearing Research* 60(10): 3027-38.

Luo, Yi, Zhuo Chen, and Nima Mesgarani. 2018. "Speaker-Independent Speech Separation with Deep Attractor Network." *IEEE/ACM Transactions on Audio Speech and Language Processing* 26(4): 787-96.

Michel, Ulf. 2006. "History of Acoustic Beamforming." *Proceedings of the Berlin Beamforming Conference*: 1-17, http://elib.dlr.de/47021/1/BeBeC_2006_Paper_Michel.pdf (Nov. 27, 2019).

Miran, Sina et al. 2018. "Real-Time Tracking of Selective Auditory Attention From M/EEG: A Bayesian Filtering Approach." *Frontiers in Neuroscience* 12. http://journal.frontiersin.org/article/10.3389/fnins.2018.00262/full (Nov. 27, 2019).

Mobin, Shariq, and Bruno Olshausen. 2019. "Auditory Separation of a Conversation from Background via Attentional Gating." http://arxiv.org/abs/1905.10751 (Nov. 27, 2019).

O'Sullivan, James A, et al. 2015. "Attentional Selection in a Cocktail Party Environment Can Be Decoded from Single-Trial EEG." *Cerebral Cortex* 25(7): 1697-1706. https://academic.oup.com/cercor/article-lookup/doi/10.1093/cercor/bht355 (Nov. 27, 2019).

Pichora-Fuller, M. Kathleen et al. 2016. "Hearing Impairment and Cognitive Energy: The Framework for Understanding Effortful Listening (FUEL)." In *Ear and Hearing*, Lippincott Williams, and Wilkins, 5S-27S.

Shield, Bridget. 2006. *EVALUATION OF THE SOCIAL AND ECONOMIC COSTS OF HEARING IMPAIRMENT A REPORT FOR HEAR-IT.*

Sim, Sangik, and Jinsook Kim. 2019. "The Review of Hearing Aid Satisfaction and Market Trends in the USA Based on Marketrak." *Audiology and Speech Research* 15(1): 11-22.

Tamamori, Akira et al. 2017. "Speaker-Dependent WaveNet Vocoder Speaker-Dependent WaveNet Vocoder." (October).

van de Rijt, L., van Wanrooij, M. M., Snik. A., Mylanus, E., van Opstal, A. J., & Roye, A. (2018). Measuring Cortical Activity During Auditory Processing with Functional Near-Infrared Spectroscopy. Journal of hearing science, 8(4), 9-18, https://doi.org/10.17430/1003278

I claim:

1. A hearing assistance device, comprising:
a body configured to engage a user's ear;
at least one ear sensor mounted to said body for obtaining at least one biosignal indicative of a user's attention, the at least one biosignal being chosen from the group consisting of at least one of: an electroencephalogram (EEG) signal, an electrooculogram (EOG) signal, an electromyogram (EMG) signal, an accelerometer signal, a gyroscope signal, and a magnetometer signal;
at least one microphone for collecting at least one environmental auditory signal; and
a processing unit adapted to:
process said at least one environmental auditory signal to determine a plurality of separated sound signals corresponding to multiple sound sources in an environment;
use the at least one biosignal to determine which of the plurality of separated sound signals to which the user is attentive in real-time;
integrate horizontal and vertical angles of a gaze of the user derived from the EOG signal with an angle of head rotation computed using the accelerometer signal, the gyroscope signal, and the magnetometer signal; and
estimate an angle of neck orientation relative to a trunk of the user using the EMG signal to compute a gaze-head-neck relative orientation angles in a fixed coordinate system.

2. The hearing assistance device of claim 1, wherein the plurality of separated sound signals are integrated with signals from an electronic device or system to provide a comprehensive understanding of the user and the environment; and
wherein said integration is performed using a sensor fusion method.

3. The hearing assistance device of claim 2, wherein the sensor fusion method comprises a Kalman filter.

4. The hearing assistance device of claim 1, wherein the at least one biosignal is used to determine, in real time, at least one of an auditory attention of the user, a visual attentional direction of the user and physical orientations of a head, the gaze, and the trunk of the user.

5. The hearing assistance device of claim 4, wherein the at least one biosignal comprises the EEG signal, and the EEG signal is used as input into at least one of a linear model and a non-linear model to determine at least one of the auditory attention of the user and the separated sound signals from the environmental auditory signal.

6. The hearing assistance device of claim 5, wherein the at least one of the linear model and the non-linear model is applied in isolation or in combination with beamforming-based speech enhancement techniques to the at least one environmental auditory signal corresponding to multiple sound sources in the environment to identify the plurality of separated sound signals.

7. The hearing assistance device of claim 1, wherein the at least one ear sensor comprises at least one of an in-ear sensor and an around-ear sensor used to obtain the at least one biosignal chosen from the group consisting of the EEG signal, the EOG signal and the EMG signal, and wherein said obtaining the at least one biosignal chosen from the group consisting of the EEG signal, the EOG signal and the EMG signal comprises obtaining a change in electrical potential of the user via a non-invasive recording from the at least one ear sensor comprising a combination of at least one of in-ear sensors and around-ear sensors.

8. The hearing assistance device of claim 1, wherein said at least one microphone comprises an array of microphones.

9. A hearing system comprising at least two hearing assistance devices according to claim 1, wherein the at least one biosignal is collected from sensors in or around both a right ear and a left ear of the user and at least one of signals from the right ear and/or signals from the left ear are used as input into at least one of a linear model and/or a non-linear model to identify an eye gaze of the user.

10. The hearing system of claim 9, further comprising a processor configured to provide an EOG control signal for controlling a function of said at least two hearing assistance devices based on said EOG control signal derived from the at least one of the linear model and the non-linear model to determine a horizontal movement and a vertical movement of an eye of the user.

11. The hearing assistance device of claim 1, further comprising a head orientation sensor for determining a relative orientation between the gaze, a head, and the trunk of the user.

12. The hearing assistance device of claim 1, wherein the separated sound signals are integrated with signals from an electronic device or system to provide a comprehensive understanding of the user and the environment; said integration being performed using a sensor fusion method for integrating a combination of at least one of auditory attention data, gaze direction data, gaze-head-trunk orientation data, location data, sound data, separated sounds, raw EEG signals, raw EOG signals, raw EMG signals, inertial data, and signals from external electronic devices that provide additional information concerning the environment of the user to identify and provide a focus of attention of the user and perform other attention-related tasks.

13. The hearing assistance device of claim 12, wherein the sensor fusion method is used to at least one of: reduce drift, increase robustness, and denoise at least one of a speech signal and the raw EOG signals.

14. The hearing assistance device of claim 12, wherein the additional information concerning the environment of the user comprises visual data.

15. The hearing assistance device of claim 1, further comprising other biopotential sensing modalities, including one or more of functional near infrared spectroscopy (fNIRS), magnetoencephalography (MEG), optical pumped magnetoencephalography (OP-MEG), giant magnetoimpedance (GMI), and functional ultrasound (fUS), wherein the processing unit is adapted to process one or more of fNIRS, MEG, OP-MEG, GMI, fUS, EEG, EOG, EMG, accelerometer, gyroscope, magnetometer and auditory signals to:
determine in real time an auditory attention of the user;
determine a visual attentional direction of the user; and
determine physical orientations of a head, the gaze, and the trunk of the user; and
wherein the hearing assistance device is configured to obtain one or more of fNIRS, MEG, OP-MEG, GMI, fUS, EEG, EOG, EMG, accelerometer, gyroscope, and magnetometer signals of the user indicative of the attention of the user.

16. A computer-implemented method for identifying a sound which is a subject of a user's attention, comprising:
measuring at least one biosignal of the user, the at least one biosignal being chosen from the group consisting of at least one of: an electroencephalogram (EEG) signal, an electrooculogram (EOG) signal, an electromyogram (EMG) signal, an accelerometer signal, a gyroscope signal, and a magnetometer signal;
collecting at least one environmental auditory signal;
performing a sound-separation process on the at least one environmental auditory signal to identify a plurality of separated sound signals corresponding to different environmental sounds;
using the at least one biosignal to determine which one of the plurality of separated sound signals to which the user is attentive;
integrating horizontal and vertical angles of a gaze of the user derived from the EOG signal with an angle of head rotation computed using the accelerometer signal, the gyroscope signal, and the magnetometer signal; and
estimating an angle of neck orientation relative to a trunk of the user using the EMG signal to compute a gaze-head-neck relative orientation angles in a fixed coordinate system.

17. The method of claim 16, wherein the at least one biosignal is used to determine, in real time, at least one of an auditory attention of the user, a visual attentional direction of the user and physical orientations of a head, a gaze, and a trunk of the user.

18. The method of claim 17, wherein said performing the sound-separation process to at least one environmental auditory signal from multiple sound sources to derive the plurality of separated sound signals comprises: applying neural-network-based speech-separation processing to the environmental auditory signal from the multiple sound sources to derive the plurality of separated sound signals, and wherein the neural-network-based sound-separation processing is applied to the environmental auditory signal from the multiple sound sources in isolation or in combination with the EEG signal recorded from at least one of a left ear and a right ear of the user.

19. The method of claim 18, further comprising: selecting at least one given signal from the separated sound signals, processing the at least one given signal, including performing one or more of: selecting at least one of a plurality of extracted beamformed signals obtained from beamforming-based speech enhancement techniques, amplifying the at least one of a plurality of extracted beamformed signals in a direction of attended sound sources, and attenuating at least one non-selected signal from the plurality of separated sound signals.

20. The method of claim 16, further comprising: selecting at least one given signal from the separated sound signals, processing the at least one given signal based on a selected sound source derived from an auditory attention identification method, including performing one or more of: amplifying the at least one given signal, or suppressing at least one of non-selected sound signals from the plurality of separated sound signals.

* * * * *